US012158450B2

(12) United States Patent
Kumar et al.

(10) Patent No.: US 12,158,450 B2
(45) Date of Patent: Dec. 3, 2024

(54) SYSTEM AND METHOD FOR DEFORMING A SPECIMEN COMPRISING TISSUE OR CELLS AND FOR MEASURING AND RECORDING THE DEFORMATION OF THE SPECIMEN

(71) Applicant: Ohio State Innovation Foundation, Columbus, OH (US)

(72) Inventors: Bharat Kumar, Columbus, OH (US); Matthew Reilly, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 1234 days.

(21) Appl. No.: 16/399,866

(22) Filed: Apr. 30, 2019

(65) Prior Publication Data

US 2019/0339179 A1 Nov. 7, 2019

Related U.S. Application Data

(60) Provisional application No. 62/665,154, filed on May 1, 2018.

(51) Int. Cl.
*G01N 3/08* (2006.01)
*C12M 1/00* (2006.01)
(Continued)

(52) U.S. Cl.
CPC ............. *G01N 3/08* (2013.01); *C12M 23/10* (2013.01); *C12M 23/50* (2013.01); *C12M 35/04* (2013.01);
(Continued)

(58) Field of Classification Search
USPC ...................................... 435/283.1
See application file for complete search history.

(56) References Cited

U.S. PATENT DOCUMENTS

| 6,057,150 A * | 5/2000 | Lee ................. C12M 23/48 435/297.5 |
| 2003/0009178 A1 * | 1/2003 | Fields ............... A61B 90/02 606/132 |

(Continued)

OTHER PUBLICATIONS

Beca, Bogdan. "A Platform for High-throughput Mechanobiological Stimulation of Engineered Microtissues". 2012. https://tspace.library.utoronto.ca/bitstream/1807/32525/1/Beca_Bogdan_201206_MASc_thesis.pdf (Year: 2012).*

(Continued)

*Primary Examiner* — Holly Kipouros
*Assistant Examiner* — Nathan G Esperon
(74) *Attorney, Agent, or Firm* — Thomas | Horstemeyer, LLP (57) ABSTRACT

A system and method are provided for applying mechanical strain to a specimen of tissues and/or cells, for measuring the deformation of the specimen caused by the mechanical strain and for recording the deformation history for the specimen. The system comprises a specimen holder configured to hold a specimen and a strain-inducing apparatus coupled to the specimen holder and configured to apply a straining displacement of a preselected magnitude in at least a first preselected direction to the specimen to strain the specimen in a preselected manner. A measurement tool of the system measures the deformation of the specimen caused by the mechanical strain and a recording tool of the system records the deformation history for the specimen in memory.

15 Claims, 11 Drawing Sheets

(51) Int. Cl.
  *C12M 1/22*    (2006.01)
  *C12M 1/36*    (2006.01)
  *C12M 1/42*    (2006.01)
  *G01N 3/06*    (2006.01)
  *C12N 5/079*   (2010.01)

(52) U.S. Cl.
  CPC ............ *C12M 41/48* (2013.01); *G01N 3/068* (2013.01); *C12N 5/0621* (2013.01)

(56) References Cited

U.S. PATENT DOCUMENTS

| | | | | |
|---|---|---|---|---|
| 2008/0166796 | A1* | 7/2008 | Quinn | C12M 25/02 435/289.1 |
| 2011/0172683 | A1* | 7/2011 | Yoo | A61B 17/322 606/151 |
| 2015/0101418 | A1* | 4/2015 | Campbell | G01N 3/08 73/826 |
| 2018/0164278 | A1* | 6/2018 | Meckel | C12M 23/46 |
| 2019/0390152 | A1* | 12/2019 | Li | C12M 41/48 |

OTHER PUBLICATIONS

Majd. "A Novel Method of Dynamic Culture Surface Expansion Improves Mesenchymal Stem Cell Proliferation and Phenotype" (Year: 2009).*

Kumar, et al., "Maintaining Epithelial Cell Viability in Whole Lens Cultures ex vivo", The Ohio State University, College of Engineering, Presentation, 3639, Poster B0198, May 9, 2017.

* cited by examiner

Table 1: Cell Viability and Proliferation Under Varying Strain Regimes

| Strain | Viability Index | Proliferation Index (%) | N |
|---|---|---|---|
| 0% | 1.00±0.00 | 9.56±1.59 | 7 |
| 6% | 1.15±0.23 | 15.85±1.39 | 3 |
| 12% | 1.24±0.12 | 26.93±8.96 | 4 |

SYSTEM AND METHOD FOR DEFORMING A SPECIMEN COMPRISING TISSUE OR CELLS AND FOR MEASURING AND RECORDING THE DEFORMATION OF THE SPECIMEN

CROSS-REFERENCE TO RELATED APPLICATIONS

The present application is a nonprovisional PCT international application that claims the benefit of and priority to the filing date of U.S. provisional application Ser. No. 62/665,154 filed on May 1, 2018 and entitled "EXPANDING RING DEVICE FOR THE EQUIBIAXIAL DEFORMATION OF SUBSTRATE," which is hereby incorporated by reference herein in its entirety.

BACKGROUND

The lens of the eye grows continuously throughout life, leading to age-related changes in geometry, as well as optical and mechanical performance. The ability to modulate the rate of lens growth is therefore an appealing approach to preventing age-related conditions and diseases in the lens.

The specific causes of lens growth throughout an individual's lifetime are unknown. One proposed explanation is that mechanical cues from accommodation activate mechanotransduction pathways and upregulate lens epithelial cell (LEC) proliferation.

A need exists for a way to determine whether such mechanical cues from accommodation increase the proliferation rate of LECs.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

The present disclosure is directed to a system and method for applying mechanical strain to a tissue specimen or a specimen comprising a plurality of cells, for measuring the deformation of the tissue or cells specimen caused by the mechanical strain and for recording the deformation history for the tissue or cells specimen. The system comprises a specimen holder configured to hold a tissue specimen or a specimen comprising a plurality of cells in a culture dish and a strain-inducing apparatus coupled to the specimen holder and configured to apply a straining displacement of a preselected magnitude in at least a first preselected direction to the specimen holder. At least a portion of the strain that is applied to the specimen holder is transferred to and applied to the specimen to strain the specimen in a preselected manner. The system comprises a measurement tool for measuring the deformation of the specimen caused by the strain and a recording tool for recording the deformation history of the specimen in memory. The recorded deformation history and the effect that the application of mechanical strain over time has on the specimen can be studied to help determine its effect, such as the effect that it may have on LEC proliferation, for example.

In the following detailed description, a few illustrative, or representative, embodiments are described to demonstrate the inventive principles and concepts. For purposes of explanation and not limitation, representative embodiments disclosing specific details are set forth in order to provide a thorough understanding of an embodiment according to the present disclosure. However, it will be apparent to one having ordinary skill in the art having the benefit of the present disclosure that other embodiments that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "specimen," as that term is used herein, is intended to denote either living tissue and/or living cells. For example, in some cases the specimen comprises soft tissue, such as all or a portion of the lens of a human eye disposed on a suitable specimen holder. In other cases, the specimen comprises a plurality of cells disposed on a suitable specimen holder.

The term "memory" or "memory device," as those terms are used herein, are intended to denote a non-transitory computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor," "processing logic," or "controller," as those terms are used herein, encompass an electronic component that is able to execute a computer program, portions of a computer program or computer instructions and that is implemented in hardware, software or firmware, or a combination thereof. References herein to a computer comprising "a processor," "processing logic," or a "controller" should be interpreted as a computer having one or more processors, processing cores, or controllers. The processor or controller may, for instance, be a multi-core processor or controller. A processor or controller may also refer to a collection of processors or controllers within a single computer system or distributed amongst multiple computer systems.

Exemplary, or representative, embodiments will now be described with reference to FIGS. 1A-10, in which like reference numerals represent like components, elements or features. It should be noted that features, elements or components in the figures are not intended to be drawn to scale, emphasis being placed instead on demonstrating inventive principles and concepts.

Figure 1A:
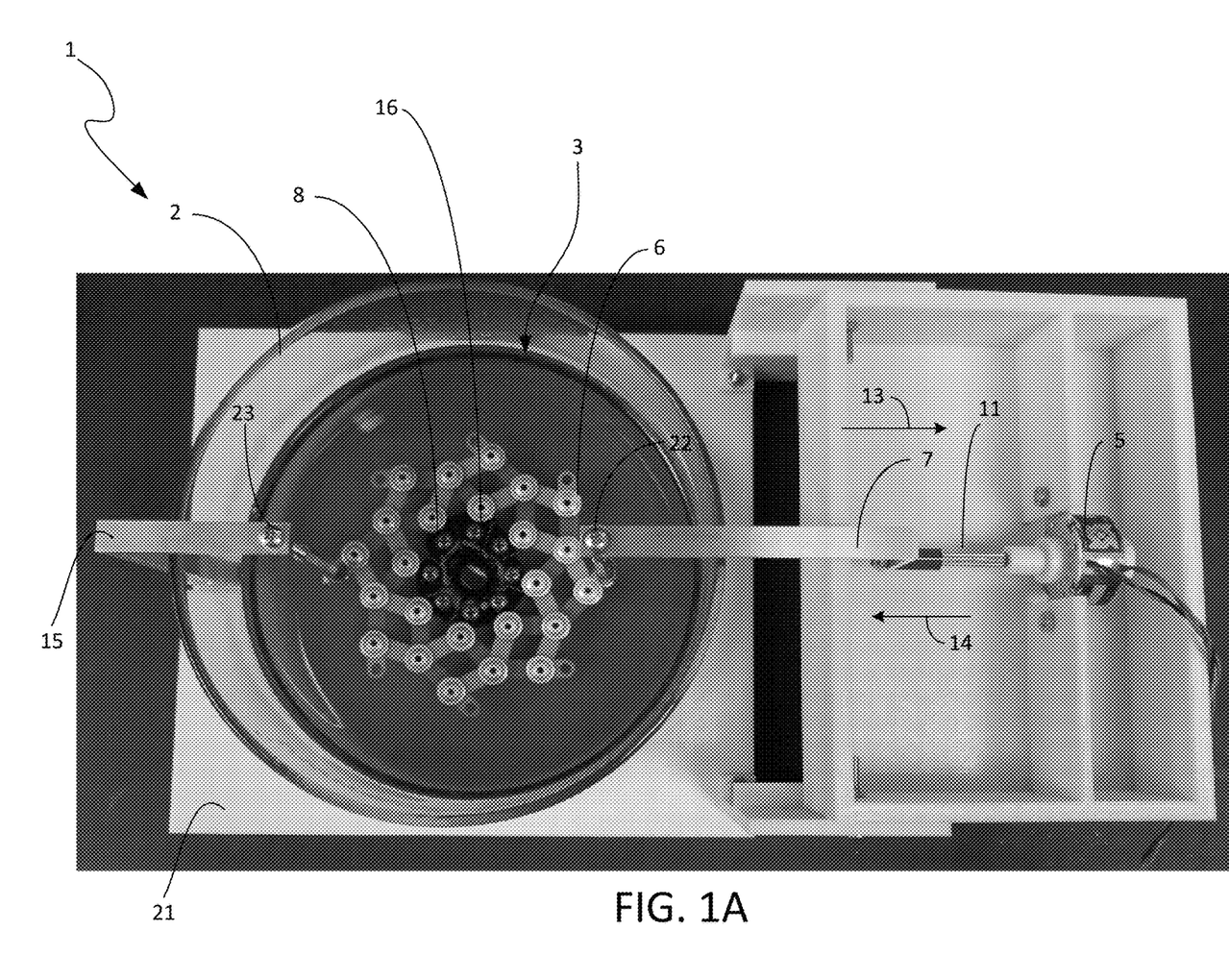
FIG. 1A-1C illustrate the system in accordance with an embodiment.
Figure 1B:
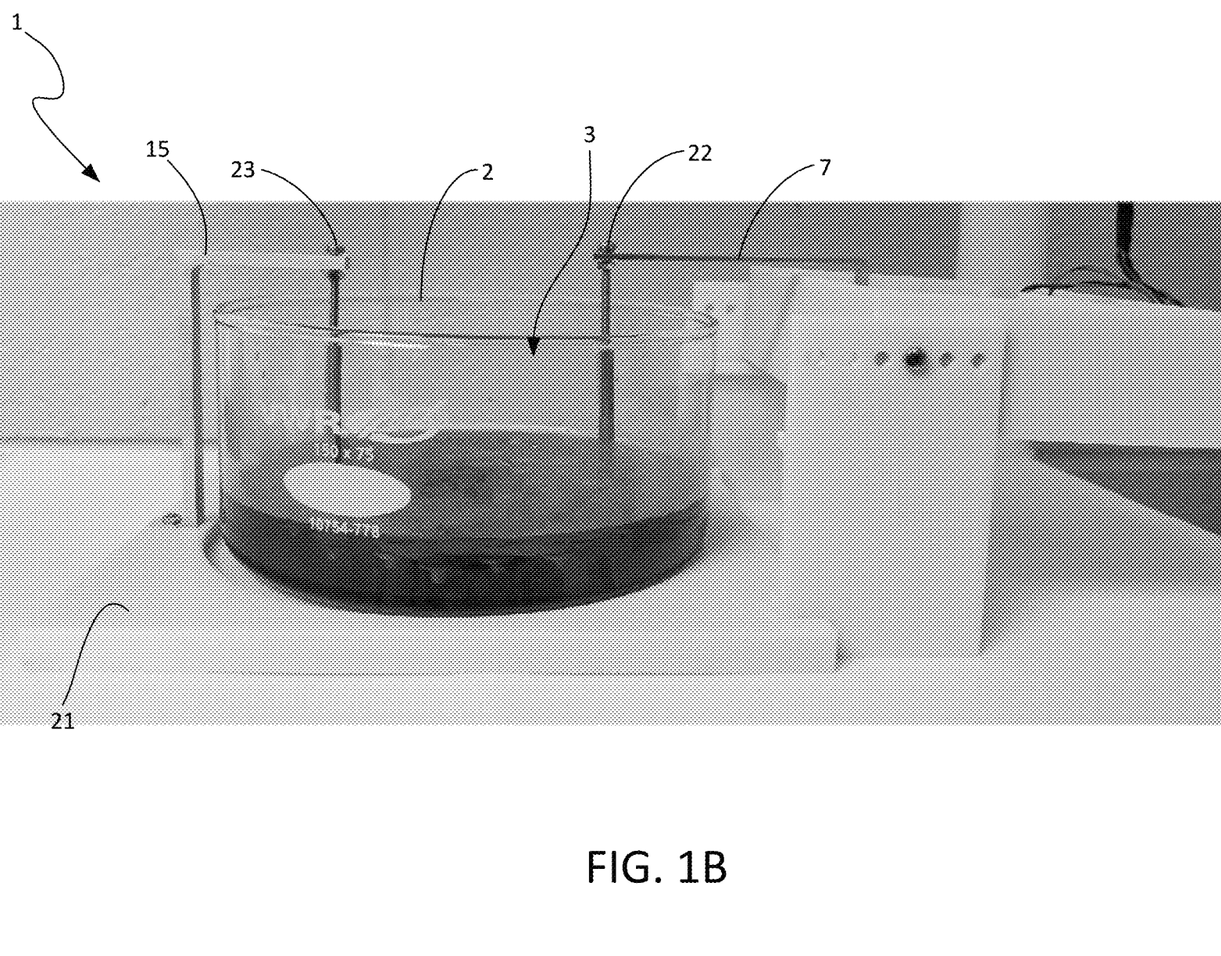
Figure 1C:
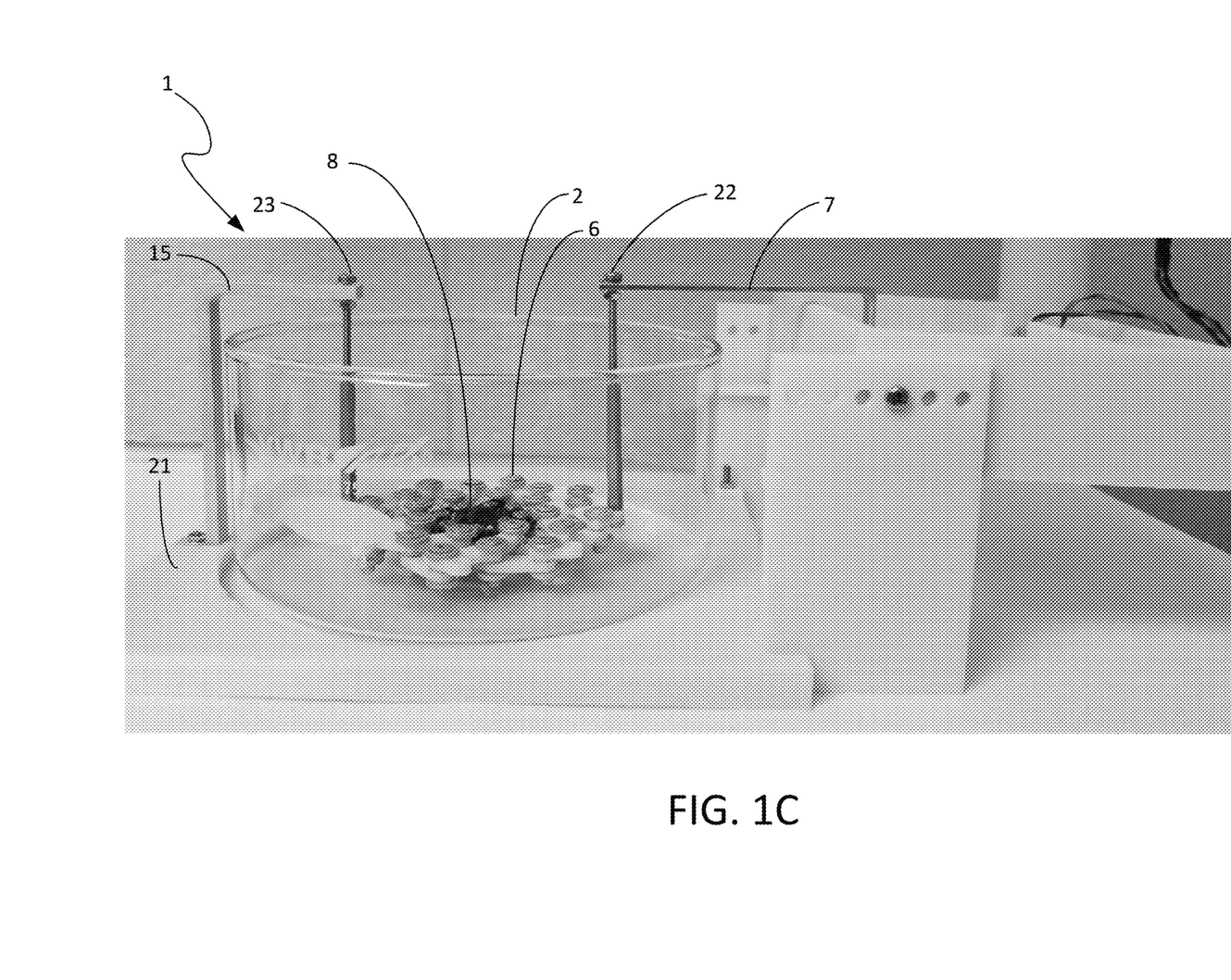

FIGS. 1A and 1B show, respectively, top and side perspective views of the system 1 in accordance with a representative embodiment. A culture dish 2 of the system 1 contains a liquid medium 3 for substrate submersion. FIG. 1C shows the same side perspective view of the system 1 shown in FIG. 1B, except that the liquid medium 3 shown in FIG. 1B is not shown in FIG. 1C. The term "substrate," as that term is used herein, refers to a specimen.

Figure 2A:
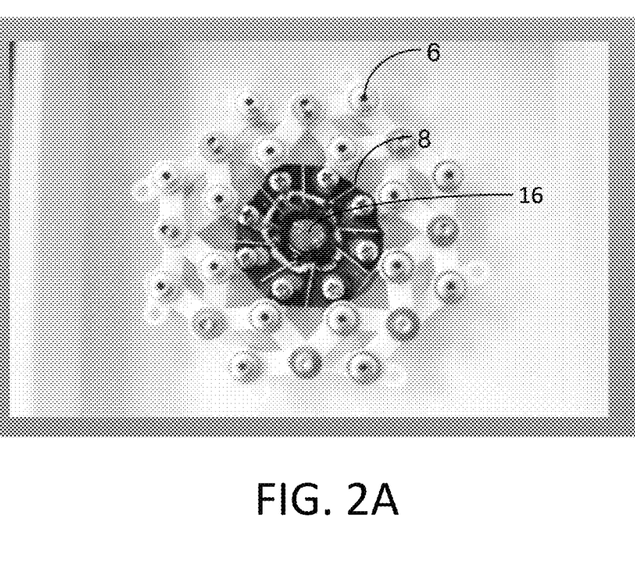
FIGS. 2A and 2B show top views of the expanding ring structure of the system shown in FIG. 1 in the unstretched and stretched configurations, respectively.
Figure 2B:
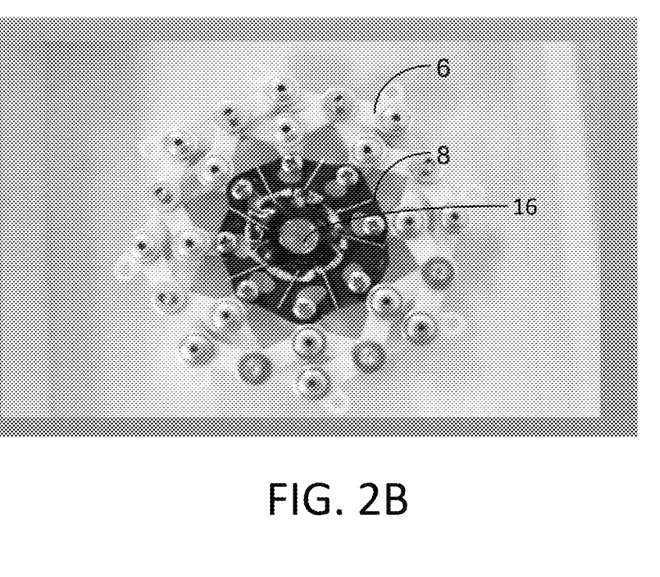

In accordance with this embodiment, the specimen holder 8 is the aforementioned elastomeric, generally ring-shaped device, which is better seen in FIGS. 2A and 2B. In other embodiments, such as those in which the specimen comprises a plurality of cells, but not tissue, the specimen holder may comprise a synthetic substrate, such as a silicone substrate, for example. For ease of discussion, it will be assumed that the specimen holder comprises the elastomeric, generally ring-shaped device, but it will be understood that the inventive principles and concepts are not limited to the specimen holder being made of any particular material or having any particular shape, size of configuration.

A strain-inducing apparatus of the system 1 mechanically couples with the specimen holder 8. The strain-inducing apparatus comprises a motor 5, a control circuit (not shown), an expanding ring structure 6, and a linkage 7. A linear drive 11 of the motor 5 is mechanically coupled to the linkage 7. The linkage 7 is mechanically coupled with the expanding ring structure 6 on one side of the expanding ring structure 6. On the opposite side of the expanding ring structure 6, the expanding ring structure 6 is mechanically coupled with a bracket 15, which is mechanically coupled with a base 21 of the system 1. First and second coupling devices 22 and 23, respectively, mechanically couple the linkage 7 and the bracket 15, respectively, to opposite sides of the expanding ring structure 6.

FIGS. 2A and 2B show top views of the expanding ring structure 6 in accordance with a representative embodiment in the unstretched and stretched states, respectively. The motor 5 (FIG. 1A) is configured to operate the linear drive 11 (FIG. 1A) to impart motion to the linear drive 11 in directions 13 and 14 (FIG. 1A). Direction 13 is away from a central axis of the elastomeric, generally ring-shaped device 8 (FIGS. 2A and 2B) substantially perpendicular to the central axis of the elastomeric, generally ring-shaped device 8. Direction 14 is toward the central axis of the elastomeric, generally ring-shaped device 8 substantially perpendicular to the central axis of the elastomeric, generally ring-shaped device 8. The control circuit (not shown) controls the motor 5 to thereby control the motion of the linear drive 11.

Movement of the linear drive 11 in the direction 13 causes the expanding ring structure 6 to expand radially, which stretches the elastomeric, generally ring-shaped device 8 radially. Expansion of the expanding ring structure 6 radially stretches the specimen 16 (FIGS. 2A and 2B) that is attached to the expanding ring structure 6 radially. Movement of the linear drive 11 in direction 14 causes the expanding ring structure 6 to contract radially to its resting state, which causes the elastomeric, generally ring-shaped device 8 to contract to its resting state. This, in turn, removes the strain from the specimen 16 and allows it to return to its resting state, which is usually the state it was in before it was stretched.

Figure 3A:
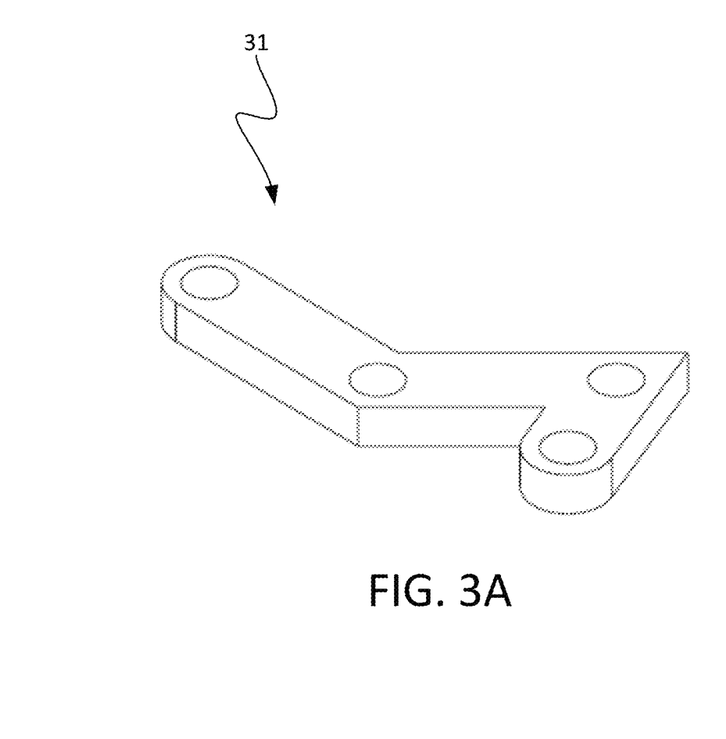
FIGS. 3A and 3B show top perspective views of the inner and outer struts 31 and 32, respectively.
Figure 3B:
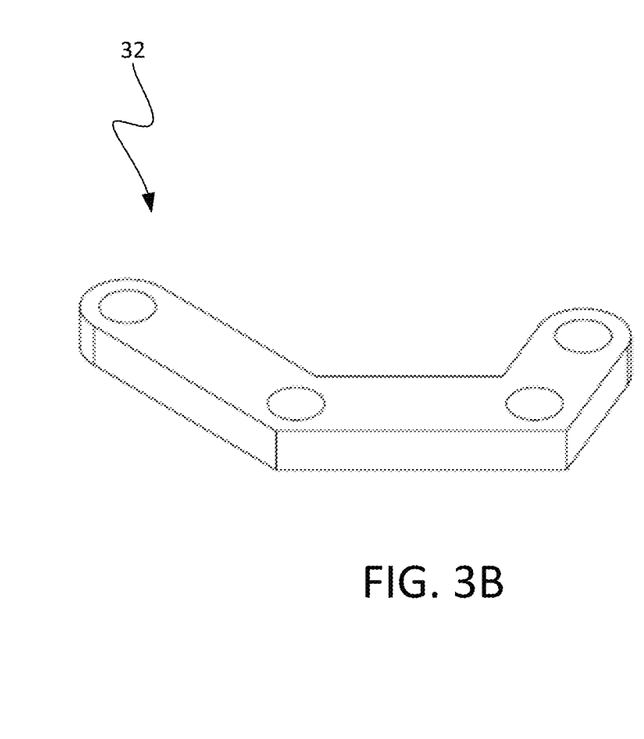

The expanding ring structure 6 comprises a plurality of inner struts and a plurality of outer struts that are mechanically coupled together in a particular way to produce the above-described radially expanding and contracting actions that radially stretch and relax the specimen, respectively. FIGS. 3A and 3B show top perspective views of the inner and outer struts 31 and 32, respectively. Each of the inner struts is mechanically coupled with the elastomeric, generally ring-shaped device 8 and with at least one of the outer struts 32, as shown in FIGS. 2A and 2B. A first one of the outer struts 32 is mechanically coupled with an end of the linkage 7 via the first coupling device 22. A second one of the outer struts 32 on an opposite side of the expanding ring structure 6 is mechanically coupled with the bracket 15 via the second coupling device 23. Due to this configuration, the expanding ring structure 6 converts the linear displacement produced by the linear drive 11 into radial displacements that are exerted on the elastomeric, generally ring-shaped device 8.

In the embodiment shown in FIGS. 2A and 2B, the expanding ring structure 6 is coupled to the elastomeric, generally ring-shaped device 8 at points on the periphery of the elastomeric, generally ring-shaped device 8 that are equally spaced apart from one another. Consequently, when the expanding ring structure 6 expands radially, equal displacements are applied radially outwardly away from a central axis of the elastomeric, generally ring-shaped device 8 at the points at which the expanding ring structure 6 couples with the elastomeric, generally ring-shaped device 8. This application of biaxial or multi-axial radial displacements is not always needed or desired. If the expanding ring structure 6 were to be connected to the elastomeric, generally ring-shaped device 8 at only two points that are on opposite sides of the elastomeric, generally ring-shaped device 8, i.e., at points that about 180° apart, uniaxial displacements of equal magnitude and opposite direction would be applied to the specimen 16. Thus, the system 1 can be used to apply uniaxial, biaxial or multiaxial stretching displacements to the specimen 16. As another example, If the expanding ring structure 6 were to be connected to the elastomeric, generally ring-shaped device 8 at only four points, where each point of 90° away from an adjacent point of connection (e.g., points a 0°, 90°, 180° and 270°), displacements of equal magnitude and opposite direction would be applied to the specimen 16 at 0° and 180°, and displacements of equal magnitude and opposite direction would be applied to the specimen 16 at 90° and 270°. The expanding ring structure 6 is designed to apply displacements of equal magnitude at each point of connection, but displacements of unequal magnitude can also be achieved by using connection points that are asymmetrically located. Thus, displacements having a wide range of magnitudes and directions can be applied to the specimen 16.

Also, while the representative embodiment are being described with reference to using the expanding ring structure 6, other types of strain-inducing apparatuses may be used. For example, in cases in which displacements in only two opposing directions are needed, a less complex linear displacement-inducing apparatus could be used.

Experimental Setup and Results

As indicated above, the specific causes of lens growth throughout an individual's lifetime are unknown, but one proposed explanation is that mechanical cues from accommodation activate mechanotransduction pathways and upregulate LEC proliferation. The following experiment was performed using the system 1 to stretch a lens to test the hypothesis that the proliferation rate of LECs increases with the extent of equatorial stretching experienced by the lens.

Pairs of freshly enucleated porcine eyes were dissected and the crystalline lens was removed while attached to the ciliary body and a portion of the sclera. The sclera was attached to the elastomeric, generally ring-shaped device 8 (FIGS. 2A and 2B). One lens from each pair was then placed in a well plate while its fellow lens was stretched by the system 1 shown in FIGS. 1a-1C to a static equatorial strain (% change in equatorial diameter) of either 6% or 12%. Culture media included vitreous humor and EdU. Lenses were harvested after 24 hours.

Figure 4:
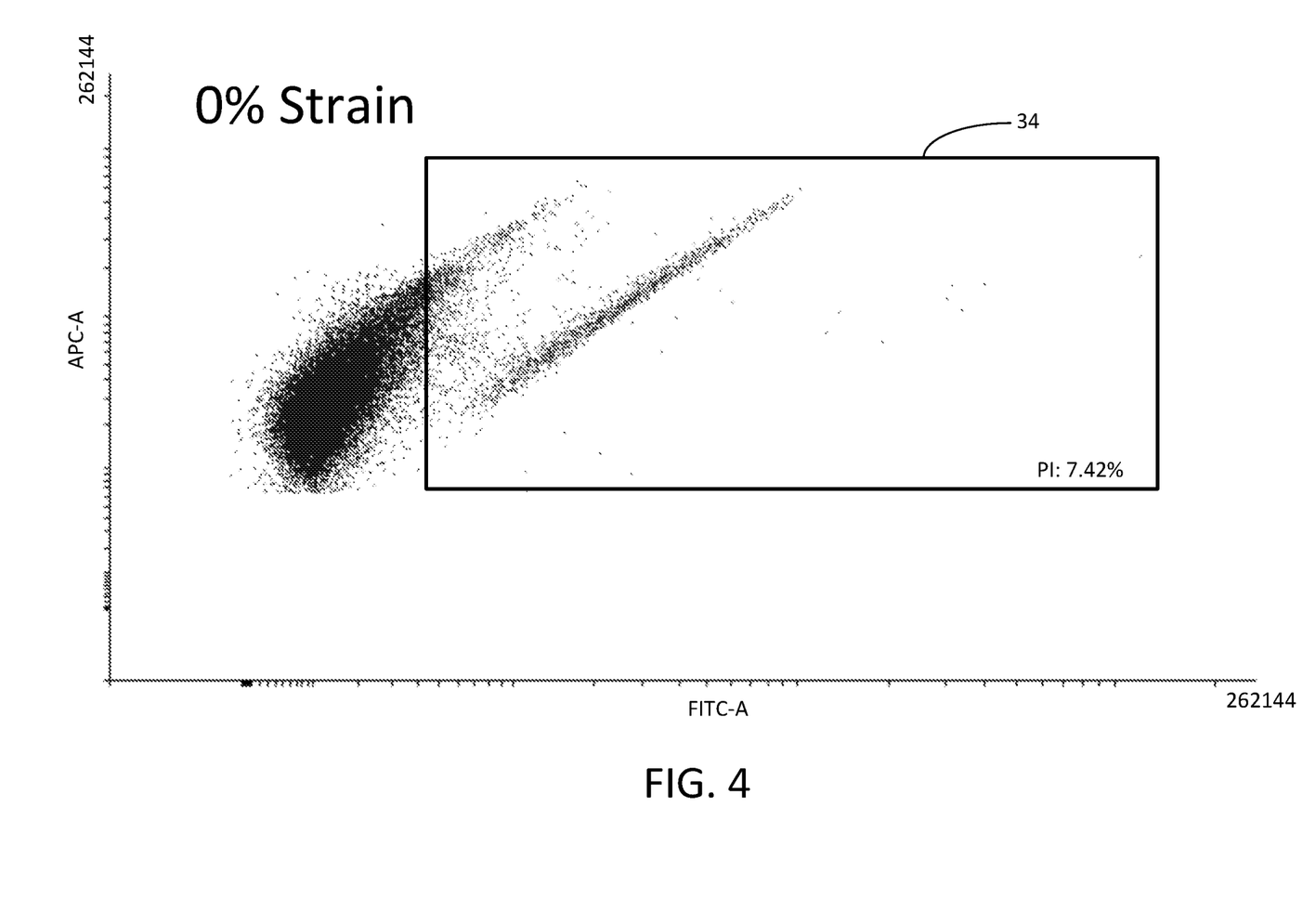
FIGS. 4, 5 and 6 show the proliferative capacity for the lenses cultured for 24 hours at 0% strain, 6% strain and 12% strain, respectively.
Figure 5:
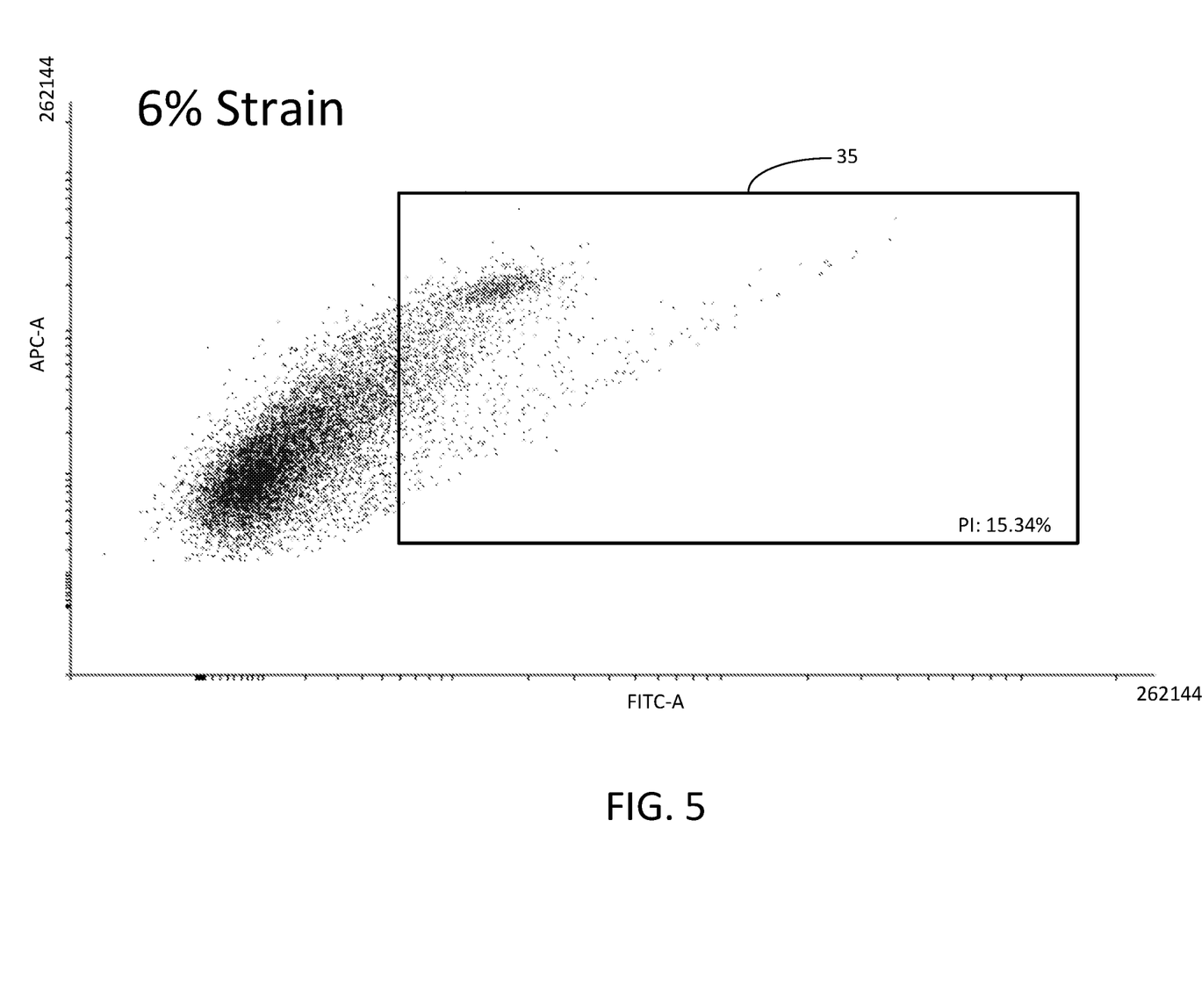
Figure 6:
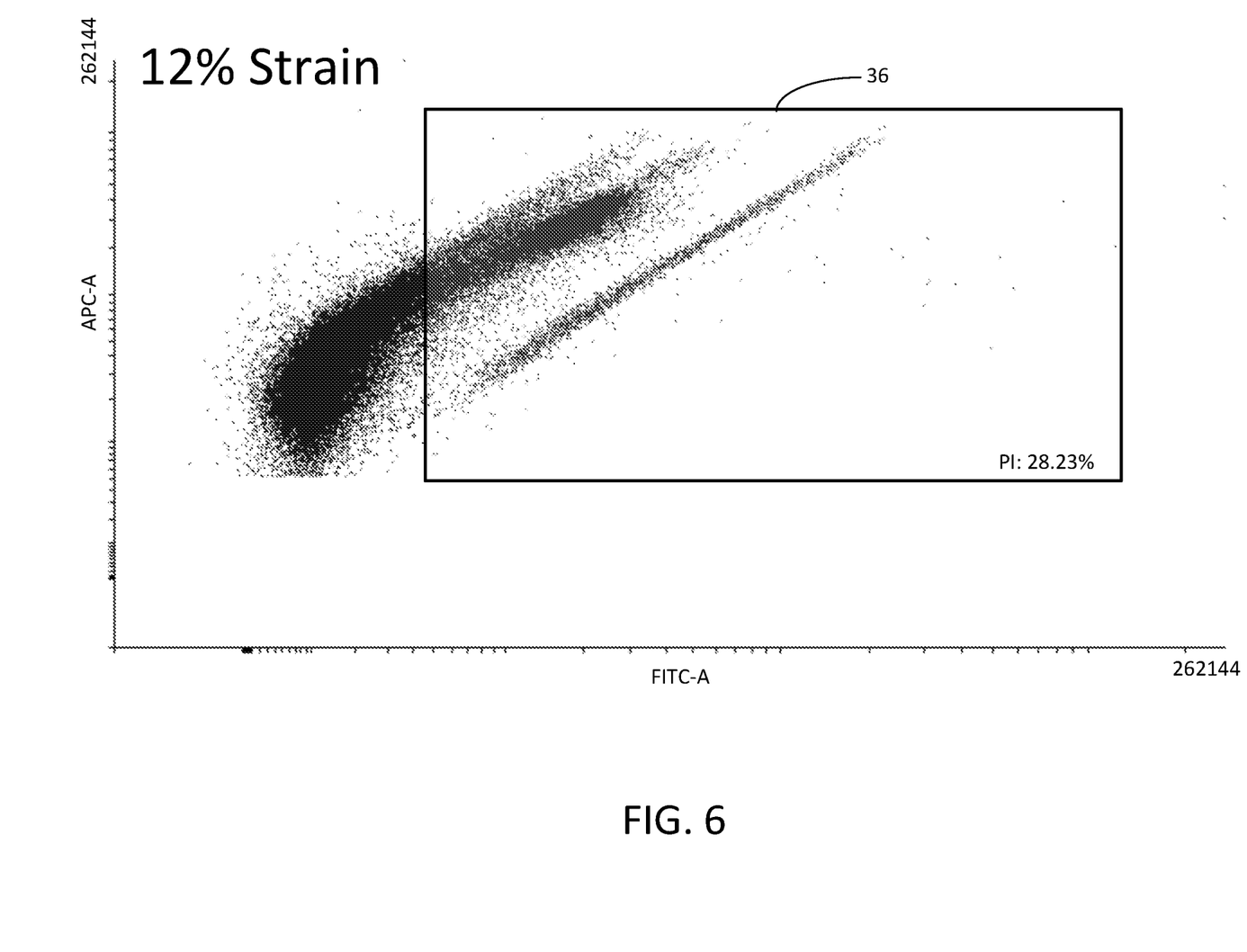

LEC viability was quantified using a hemocytometer after removing the fiber cell bundle and trypsinizing the anterior lens capsule. Viable cell counts from the mechanically strained lenses were normalized to data from the fellow 0% strain lens. The proliferative capacity of the cultured lenses were measured by staining LECs with a general nuclear stain (NucRed647) and for a proliferative marker (Alexa 488) and counting proliferating cells in a flow cytometer. FIGS. 4, 5 and 6 graphically show the proliferative capacity for the lenses cultured for 24 hours at 0% strain, 6% strain and 12% strain, respectively. The horizontal and vertical axes in FIGS. 4-6 both represent the intensity of the light emitted from a cell after a commercially-available flow cytometer shines a laser on the cell. The intensity of emitted light is proportional to how much of a fluorescent label is in the cell. The amount of label is proportional to how much of what is being tested for inside of the cell. The APC (vertical) axis is testing for DNA content, so dots higher on the axis have more DNA. The FITC (horizontal) is testing for newly synthesized DNA, which is being used to measure proliferation. The more new DNA in a cell, the more it is proliferating. Cells were counted as positive for nuclear stain (portion outside of the boxes 34, 35 and 36 in FIGS. 4, 5 and 6, respectively) or nuclear and proliferation stains (portions inside of the boxes 34, 35 and 36 in FIGS. 4, 5 and 6, respectively) based on threshold emissions derived from autofluorescence-derived thresholds. Thus, the axes show the intensity of fluorescence produced by the cells in response to the proliferative marker, FITC, and nuclear stain, APC lasers.

Figure 7:
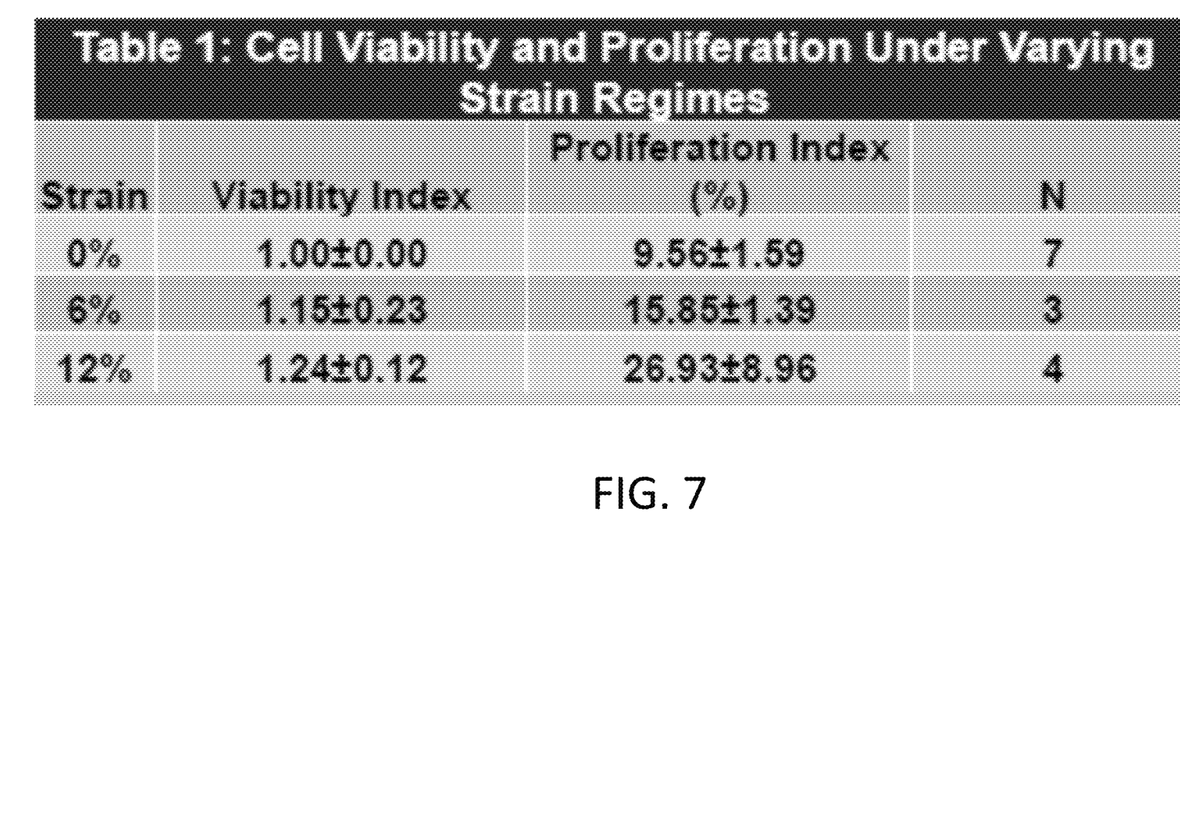
FIG. 7 shows a table that gives mean±95% confidence intervals for viability and proliferation indices.

Table 1 shown in FIG. 7 gives mean±95% confidence intervals for viability and proliferation indices. Both metrics increased in a strain-dependent manner. The strain column represents the % change in equatorial diameter of the lens compared to its unstretched state. Viability index is the number of cells harvested from the stretched lens compared to the paired unstretched control (Each pig had 2 eyes, one eye was stretched, the paired eye was unstretched and measured as a control). Proliferation index is the % of cells that tested positive for the proliferative marker out of the total number of cells analyzed using flow cytometry. N is the number of lenses in each strain group. There were seven pairs, one eye from each pair was at 0%. Of the remaining seven eyes, three eyes were stretched to 6% and four were at 12%.

Figure 8:
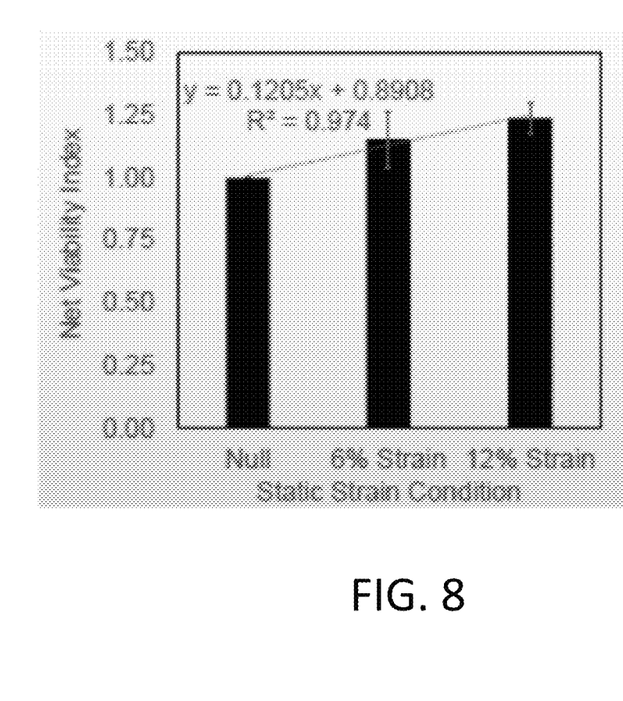
FIG. 8 is a graph that shows that the number of viable LECs increased significantly with strain amplitude after 24 hours in culture (p=0.0013).
Figure 9:
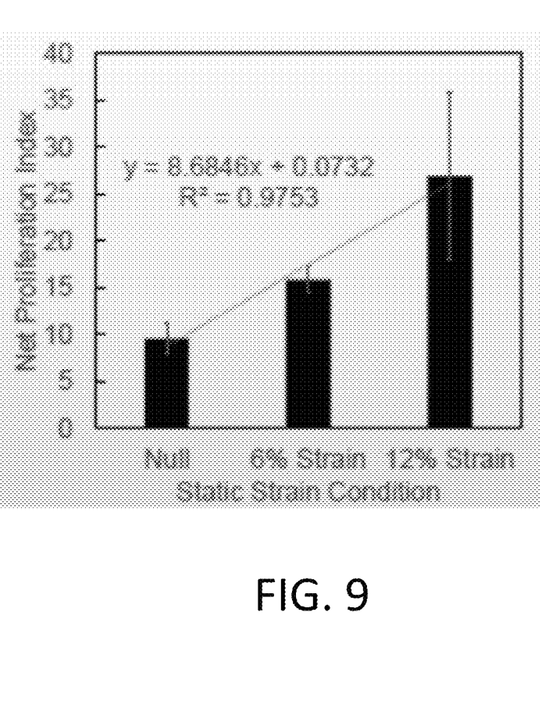
FIG. 9 is a graph that shows that the proliferation index increased significantly with strain amplitude after 24 hours in culture (p=0.0002).

FIG. 8 is a graph that shows that the number of viable LECs increased significantly with strain amplitude after 24 hours in culture (p=0.0013). FIG. 9 is a graph that shows that the proliferation index increased significantly with strain amplitude after 24 hours in culture (p=0.0002). These figures show a graphical representation of the data in Table 1 of FIG. 7. A linear regression analysis was performed (the equations on the graph). They show that both the number of cells harvested and the % of cells proliferating increase linearly with % strain.

The data obtained during the experiment indicate that mechanical strain does increase the proliferation rate of the LECs. The data also indicate that the amplitude of the strain modulates the proliferation rate of the LECs.

Figure 10:
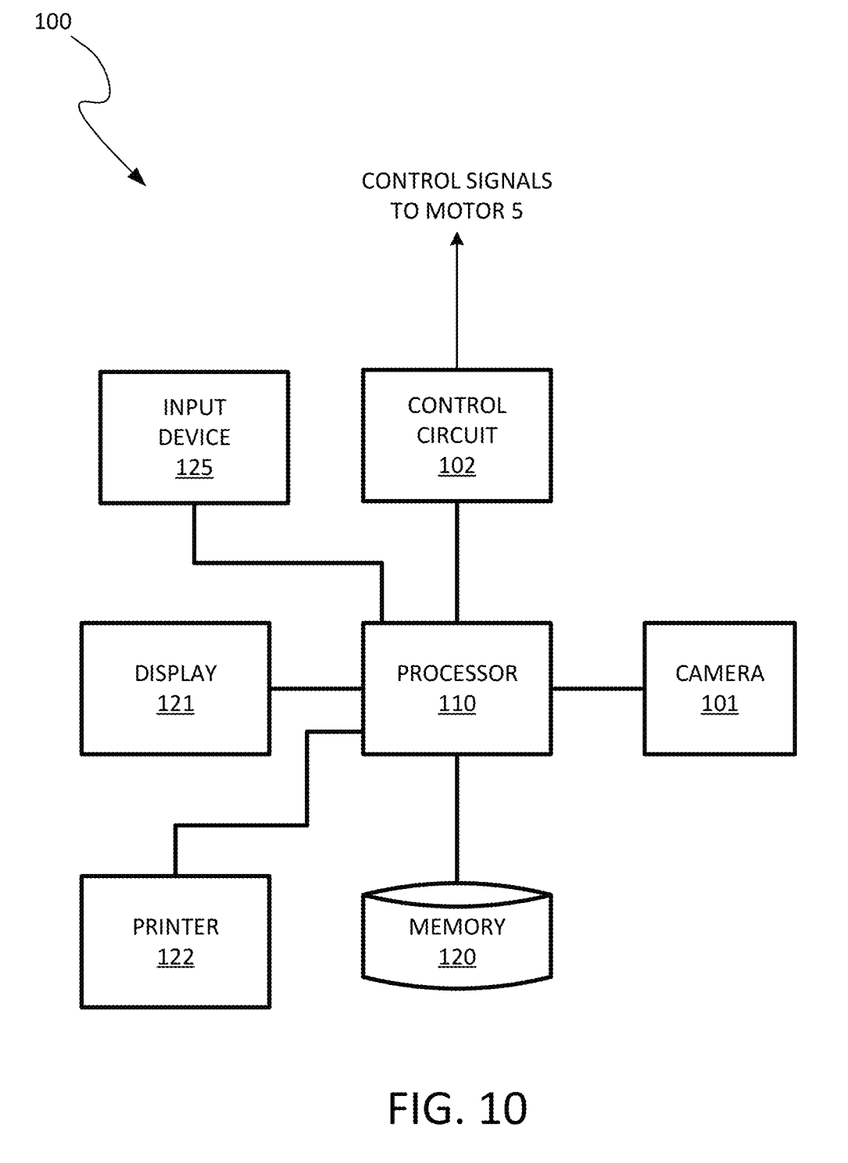
FIG. 10 is a block diagram of a computer system that is used to monitor and control the system shown in FIGS. 1A-1C applying mechanical strain to a specimen of tissue or cells.

In accordance with a representative embodiment, the extent of deformation of the specimen is determined using a camera and image processing software running on a suitable processor. FIG. 10 is a block diagram of a computer system 100 that is used to monitor and control the system 1 shown in FIGS. 1A-1C. In accordance with this representative embodiment, the computer system 100 includes a camera 101 that captures images of the specimen held in the elastomeric, generally ring-shaped device 8. The captured images are processed by a processor 110 of the system 100 to determine the extent of deformation. The processor 110 also controls a control circuit 102 that outputs control signals to the motor 5 (FIG. 1A) to control the amount of strain that the motor 5 induces and the time periods during which strain is induced. The processor 110 records the deformation history associated with the specimen in a memory device 120 of the system 100. The deformation history for a given specimen typically comprises the frequency of stretching of the specimen, the extent of stretching of the specimen, the periods of time during which the specimen remains in a stretched state and the periods of time during which the specimen remains in a resting, or unstretched, state.

In order to process the images captured by the camera 101, the processor 110 runs an image processing algorithm. In accordance with a representative embodiment, the system 1 shown in FIGS. 1A-1C includes a fiducial (not shown). The fiducial may be, for example, a device having a known size and position, such as the head of the first coupling device 22, which is a Phillips screw head. The camera 101 is typically positioned above the system 1 to have a top view similar to the view shown in FIG. 1C. The camera captures the images and forwards the images to the processor 110. The processor 110 executes the image processing algorithm that compares the size of the specimen in each captured image with the size of the fiducial captured in the image and determines the size, or diameter, of the specimen based on the size of the specimen image relative to the known size of the fiducial image.

The processor 110 also runs a logging algorithm that records the deformation history of the specimen in memory device 120. The computer system 100 may include a display device 121 and/or a printer 122 to allow the processor 110 to cause a deformation history report to be displayed and/or printed. The computer system 100 may include a display device 121 and/or a printer 122 to allow the processor 110 to cause a deformation history report to be displayed and/or printed.

The processor 110 also runs a control algorithm that allows the processor 110 to control the motor 5, which may be a stepper motor, for example, by causing the control circuit 102 to generate appropriate control signals at appropriate times. The computer system 100 may include an input device 125 such as a keyboard, for example, to allow a user to input parameters or settings to the processor 110 to apply when performing the control algorithm. For example, the parameters or settings may include the amount of strain to be applied to the specimen, the frequency with which a particular amount of strain is to be applied, the period of duration of applying particular amounts of strain, etc. The image processing algorithm can be configured to generate the control signals for controlling the control circuit 102 based on the images captured by the camera 101. For example, when the processor 110 running the image processing algorithm determines that the specimen is in a stretched state, the processor 110 may start a timer for a preselected period of time, determine when the timer has expired, and then cause the motor 5 to return the specimen to the unstretched state.

While inventive principles and concepts have been discussed mainly with reference to lens tissue specimens, the inventive principles and concepts are equally applicable to other types of tissues and cells. For example cardiovascular, skin, muscular, corneal, retinal, kidney, liver, as well as any other soft tissue specimens from the body can be used. Also, while the inventive principles and concepts have been discussed with reference to the elastomeric, generally ring-shaped device 8 being used as the specimen holder, other specimen holders may be used. For example, a modified holder would be able to produce stretching along only one direction for uniaxial stretching tests, additionally, further modifications could produce stretching in 2 perpendicular directions for biaxial stretching.

It should be emphasized that the above-described embodiments of the present invention are merely possible examples of implementations, merely set forth for a clear understanding of the principles of the invention. For example, while the experiment was described as using a system that has a particular configuration, other suitable configurations may be used. Also, while the experiment was described with reference to lenses, the inventive principles and concepts are applicable to any tissue or group of cells, including, for example, heart tissue. Many variations and modifications may be made to the above-described embodiments without departing from the scope of the invention. All such modifications and variations are intended to be included herein within the scope of this disclosure and the claims.

What is claimed is:

1. A system for applying mechanical strain to a specimen comprising one or both of tissue and cells, for measuring deformation of the specimen caused by applying the strain to the specimen and for measuring a deformation history of the specimen, the system comprising:

a culture dish having a liquid medium disposed therein;
a specimen holder configured to hold the specimen while the specimen is submerged in the liquid medium, wherein the specimen holder comprises an elastomeric ring-shaped device to which the specimen is attached;
a strain-inducing apparatus coupled to the specimen holder and configured to apply a radial straining displacement of a preselected magnitude in at least a first preselected direction to the specimen holder, the strain-inducing apparatus comprising an expanding ring structure having a plurality of interconnected struts symmetrically distributed about the specimen holder, the plurality of interconnected struts comprising first and second sets of struts, each of the first set of struts configured to mechanically couple to the elastomeric ring-shaped device at a proximal end and each of the second set of struts coupled to multiple struts in the second set of struts, wherein a distal end of a first strut of the second set of struts is attached in a fixed position and a distal end of a second strut of the second set of struts is attached to a linear drive, the distal ends of the first and second struts on opposite sides of the expanding ring structure, wherein a linear force applied by the linear drive to the second strut radially displaces all of the proximal ends of the first set of struts radially outward away from a central axis of the elastomeric ring-shaped device to produce the radial straining displacement, and wherein at least a portion of the radial straining displacement is applied to the specimen holder to produce a strain that is transferred to the specimen to strain the specimen and applied thereto;
a measurement tool configured to measure an amount by which the specimen is deformed by the strain that is applied to the specimen; and
a recording tool configured to receive an output of the measurement tool and to record a deformation history for the specimen, the deformation history including a magnitude of the strain that was applied to the specimen, a frequency at which the strain was applied to the specimen and a length of time that the strain was applied to the specimen.

2. The system of claim 1, wherein the strain-inducing apparatus is coupled to the elastomeric, ring-shaped device about a periphery of the elastomeric, ring-shaped device, and wherein said at least a first preselected direction comprises multiple directions away from the central axis of the elastomeric, ring-shaped device substantially perpendicular to the central axis of the elastomeric, ring-shaped device.

3. The system of claim 2, wherein the strain-inducing apparatus comprises:

a motor of the linear drive;
a control circuit for controlling the motor;
the expanding ring structure being configured to be controlled by the motor to transition from a radially-expanded state to a radially-contracted state, and vice versa; and
a linkage coupling the linear drive to the distal end of the second strut of the expanding ring structure.

4. The system of claim 3, wherein the motor imparts motion to the linear drive in second and third directions that are opposite one another, the linear drive being mechanically coupled to the linkage, the second direction being away from the central axis of the elastomeric, ring-shaped device substantially perpendicular to the central axis of the elastomeric, ring-shaped device, the third direction being toward the central axis of the elastomeric, ring-shaped device substantially perpendicular to the central axis of the elastomeric, ring-shaped device, and wherein motion of the linear drive in the second direction causes the expanding ring structure to transition to the radially-expanded state and to stretch the specimen outwardly, and wherein motion of the linear drive in the third direction causes the expanding ring structure to contract to the radially-contracted state to allow the specimen to relax to a resting state.

5. The system of claim 3, wherein the measurement tool comprises:
   a camera positioned and oriented to capture images of the specimen, wherein the captured images are processed to determine an extent of deformation of the specimen.

6. The system of claim 5, wherein the recording tool records the deformation history in a memory device.

7. The system of claim 6, further comprising: a display device, wherein the deformation history is displayed on the display device.

8. The system of claim 6, further comprising:
   a printer, wherein a report of the deformation history is printed by the printer.

9. The system of claim 1, wherein the strain-inducing apparatus comprises:
   a motor of the linear drive,
   a control circuit for controlling the motor,
   wherein the expanding ring structure is controlled by the motor to transition from a radially-expanded state to a radially-contracted state, and from the radially-contracted state to the radially-expanded state.

10. The system of claim 9, wherein the strain-inducing apparatus is coupled to the elastomeric, ring-shaped device about a periphery of the elastomeric, ring-shaped device, and wherein said at least a first preselected direction comprises multiple directions away from the central axis of the elastomeric, ring-shaped device substantially perpendicular to the central axis of the elastomeric, ring-shaped device.

11. The system of claim 10, wherein the motor imparts motion to the linear drive in second and third directions that are opposite one another, the second direction being away from the central axis of the elastomeric, ring-shaped device substantially perpendicular to the central axis of the elastomeric, ring-shaped device, the third direction being toward the central axis of the elastomeric, ring-shaped device substantially perpendicular to the central axis of the elastomeric, ring-shaped device, and wherein motion of the linear drive in the second direction causes the expanding ring structure to transition to the radially-expanded state and to stretch the specimen outwardly, and wherein motion of the linear drive in the third direction causes the expanding ring structure to contract to the radially-contracted state to allow the specimen to relax to a resting state.

12. The system of claim 10, wherein the measurement tool comprises:
   a camera positioned and oriented to capture images of the specimen, wherein the captured images are processed to determine an extent of deformation of the specimen.

13. The system of claim 12, wherein the recording tool records the deformation history in a memory device.

14. The system of claim 1, wherein the specimen comprises proliferating cells stimulated by the strain transferred to the specimen.

15. The system of claim 14, wherein an amplitude of the strain modulates a proliferation rate of the proliferating cells.

* * * * *